(12) United States Patent
McCusker et al.

(10) Patent No.: US 8,088,092 B2
(45) Date of Patent: *Jan. 3, 2012

(54) HIGH PRESSURE RANGE HYDROCEPHALUS VALVE SYSTEM

(75) Inventors: Daniel J. McCusker, Bridgewater, MA (US); Alan J. Dextradeur, Franklin, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/500,192

(22) Filed: Jul. 9, 2009

(65) Prior Publication Data

US 2010/0010415 A1  Jan. 14, 2010

Related U.S. Application Data

(63) Continuation of application No. 10/955,258, filed on Sep. 30, 2004, now Pat. No. 7,559,912.

(51) Int. Cl.
*A61M 5/00* (2006.01)
(52) U.S. Cl. ............................... 604/9; 604/8
(58) Field of Classification Search ............ 604/7–10, 604/264, 28, 30, 43; 606/108; 137/15.21, 137/15.22; 251/157, 162
See application file for complete search history.

(56) References Cited

U.S. PATENT DOCUMENTS

| | | |
|---|---|---|
| 3,877,137 A | 4/1975 | Hakim et al. |
| 3,886,948 A | 6/1975 | Hakim |
| 3,889,687 A | 6/1975 | Harris et al. |
| 3,924,635 A | 12/1975 | Hakim et al. |
| 3,958,562 A | 5/1976 | Hakim |
| 4,106,510 A | 8/1978 | Hakim |
| 4,261,341 A | 4/1981 | Hakim |
| 4,312,293 A | 1/1982 | Hakim |
| 4,332,255 A | 6/1982 | Hakim |
| 4,387,715 A | 6/1983 | Hakim |
| 4,443,214 A | 4/1984 | Marion |
| 4,551,128 A | 11/1985 | Hakim |
| 4,595,390 A | 6/1986 | Hakim |
| 4,608,992 A | 9/1986 | Hakim |

(Continued)

FOREIGN PATENT DOCUMENTS

JP  60-040063 A  3/1985

OTHER PUBLICATIONS

Communication from European Patent Office dated Dec. 22, 2008.

(Continued)

*Primary Examiner* — Leslie Deak
(74) *Attorney, Agent, or Firm* — Nutter McClennen & Fish LLP (57) ABSTRACT

A valve for use in a shunt system to drain fluid from one part of a patient's body to another is provided. In an exemplary embodiment, the valve is operable at a threshold pressure that is selectively adjustable up to at least about 400 mm $H_2O$ at increments in the range of about 10 mm $H_2O$ to 40 mm $H_2O$. The ability of the valve to operate at a high threshold pressure and to be adjusted at relatively small increments renders the valve particularly advantageous for use in younger hydrocephalus patients. In particular, the operating pressure of the valve can be gradually limited in small increments over a period of time to slowly force the patient's own resorption system to circulate cerebrospinal fluid. At high operating pressures of at least about 400 mm $H_2O$ shunt independence can be achieved thereby allowing the shunt to be successfully removed.

40 Claims, 4 Drawing Sheets

U.S. PATENT DOCUMENTS

| | | | |
|---|---|---|---|
| 4,615,691 | A | 10/1986 | Hakim |
| 4,673,384 | A | 6/1987 | Marion |
| 4,769,002 | A | 9/1988 | Hooven |
| 4,772,257 | A | 9/1988 | Hakim |
| 4,776,838 | A | 10/1988 | Sainte-Rose et al. |
| 4,776,839 | A | 10/1988 | Doumenis |
| 4,781,672 | A | 11/1988 | Hooven |
| 5,637,083 | A | 6/1997 | Bertrand et al. |
| 5,643,194 | A | 7/1997 | Negre et al. |
| 5,643,195 | A | 7/1997 | Drevet |
| 5,928,182 | A | 7/1999 | Kraus |
| 6,050,969 | A | 4/2000 | Kraus |
| 6,090,062 | A | 7/2000 | Sood |
| 6,371,464 | B1 | 4/2002 | Porche |
| 6,383,159 | B1 | 5/2002 | Saul |
| 6,383,160 | B1 | 5/2002 | Madsen |
| 6,514,226 | B1 | 2/2003 | Levin |
| 6,575,928 | B2 | 6/2003 | Saul |
| 2002/0022793 | A1 | 2/2002 | Bertrand |
| 2002/0026139 | A1 | 2/2002 | Bertrand et al. |
| 2002/0058901 | A1 | 5/2002 | Marion |

OTHER PUBLICATIONS

Takahashi, Y., "Withdrawal of Shunt Systems—Clinical Use of the Programmable Shunt System and its Effect on Hydrocephalus in Children", Child's Nerv. Syst. (2001), vol. 17, pp. 472-477.

Abstracts from 34th Annual Meeting of the International Society for Pediatric Neurosurgery, Taipei, Taiwan, Sep. 10-14, 2006; Child's Nerv. Syst., (2006) vol. 22, pp. 1027-1060; (Abstract on p. 1049).

Final Programme, Hydrocephalus 2006, meeting in Goteborg, Sweden; Sep. 6-9, 2006 (entire program), 122 pages; Abstract Or59.

HIGH PRESSURE RANGE HYDROCEPHALUS VALVE SYSTEM

CROSS REFERENCE TO RELATED APPLICATIONS

The present application is a continuation of U.S. patent application Ser. No. 10/955,258 filed on Sep. 30, 2004 and entitled "High Pressure Range Hydrocephalus Valve System," which is hereby incorporated by reference in its entirety.

FIELD OF THE INVENTION

The present invention relates generally to medical devices for directing bodily fluids from one region of a patient to another region, and in particular the invention relates to an adjustable implantable valve for treating hydrocephalus.

BACKGROUND OF THE INVENTION

Hydrocephalus is a condition afflicting patients who are unable to regulate cerebrospinal fluid flow through their body's own natural pathways. Produced by the ventricular system, cerebrospinal fluid (CSF) is normally absorbed by the body's venous system. In a patient suffering from hydrocephalus, the cerebrospinal fluid is not absorbed in this manner, but instead accumulates in the ventricles of the patient's brain. If left untreated, the increasing volume of fluid elevates the patient's intracranial pressure and can lead to serious medical conditions such as compression of the brain tissue and impaired blood flow to the brain.

The treatment of hydrocephalus has conventionally involved draining the excess fluid away from the ventricles and rerouting the cerebrospinal fluid to another area of the patient's body, such as the abdomen or vascular system. A drainage system, commonly referred to as a shunt, is often used to carry out the transfer of fluid. In order to install the shunt, typically a scalp incision is made and a small hole is drilled in the skull. A proximal, or ventricular, catheter is installed in the ventricular cavity of the patient's brain, while a distal, or drainage, catheter is installed in that portion of the patient's body where the excess fluid is to be reintroduced.

To regulate the flow of cerebrospinal fluid and maintain the proper pressure in the ventricles, a pump or one-way control valve can be placed between the proximal and distal catheters. Generally, the shunt systems include a valve mechanism that operates to permit fluid flow only once the fluid pressure reaches a certain threshold level. That is, fluid enters the valve only when the fluid pressure overcomes the valve mechanism's resistance to open. Some valve mechanisms permit the adjustment, or programming, of the opening pressure level, or resistance level, at which fluid flow commences. These valve mechanisms can comprise a variety of configurations. For example, the valve mechanism can be configured as a ball-in-cone as illustrated and described in U.S. Pat. Nos. 3,886,948, 4,332,255, 4,387,715, 4,551,128, 4,595,390, 4,615,691, 4,772,257, and 5,928,182, all of which are hereby incorporated by reference.

Research has shown that it may be possible to successfully remove a shunt in younger hydrocephalus patients by limiting the shunt-dependent flow of the cerebrospinal fluid. In particular, the operating pressure of a programmable valve can be gradually increased to activate regular circulation of cerebrospinal fluid. As a result of careful control of the valve pressure, once sufficient cerebral development has been achieved and the patient's intracranial pressure has been normalized, the shunt can be successfully removed. Current valves, however, do not allow the threshold pressure to be adjusted in small increments and up to a threshold pressure at which the patient's own circulation system is substantially responsible for circulating cerebrospinal fluid, i.e., a threshold pressure at which shunt independence can be achieved.

Accordingly, there is a need for a valve device that can be used to gradually increase the threshold pressure, preferably in relatively small and precise increments, thereby forcing the patient's own physiologic resorption system to compensate and eventually become shunt independent.

SUMMARY OF THE INVENTION

The present invention provides a methods and devices for treating hydrocephalus. In one embodiment, a valve for use in treating hydrocephalus is provided and it generally includes a housing having an inlet and an outlet, a valve element disposed within the housing and effective to allow fluid to flow from the inlet in the housing to the outlet in the housing when a fluid pressure at the inlet is greater than a threshold pressure of the valve element, and an adjustment mechanism that is coupled to the valve element and that is effective to selectively adjust the threshold pressure up to at least about 400 mm $H_2O$ at increments in the range of about 10 mm $H_2O$ to 40 mm $H_2O$. In an exemplary embodiment, the threshold pressure is adjustable in substantially uniform increments, and more preferably in increments of about 20 mm $H_2O$.

The valve element can have a variety of configurations and virtually any valve mechanism know in the art can be used in accordance with the present invention. The valve is preferably, however, configured to remain closed until a fluid pressure differential between the inlet of the valve and the outlet of the valve exceeds a certain selected valve opening pressure. By way of non-limiting example, suitable valve elements include a tapered pin and aperture, a sliding shutter, a shutter/gate mechanism, and a ball-in-cone construct. In one exemplary embodiment the valve element includes an aperture, a restricting element, such as a ball, disposed within the aperture and having a width or diameter greater than a width or diameter of the aperture, and a biasing member coupled to an adjustment mechanism and effective to bias the restricting element against the aperture at the threshold pressure. The biasing member can be, for example, a spring extending between the adjustment mechanism and the ball, and the adjustment mechanism can be, for example, a cam mechanism having a plurality of positions formed thereon with each position corresponding to a predetermined threshold pressure. In one exemplary embodiment, each position can be in the form of a step, and the cam can include 18 steps formed thereon.

In another exemplary embodiment, at least a portion of the aperture in the valve can be in the shape of a cone having a cone angle of at least about 70°, and more preferably about 95°, and the ball can have a diameter of at least about 0.8 mm, and more preferably about 1.2 mm. More preferably, the aperture includes a proximal cone-shaped portion adapted to seat the ball and having a chamfer formed along an edge thereof, and a distal substantially cylindrical portion. The distal substantially cylindrical portion preferably has a maximum diameter of about 0.8 mm.

In another embodiment of the present invention, a valve for use in treating hydrocephalus is provided and it includes an inlet and an outlet and a valve element in communication with the inlet and outlet and effective to allow fluid to flow from the inlet to the outlet when a fluid pressure at the inlet is greater than a threshold pressure of the valve element. The threshold pressure is preferably selectively adjustable up to a pressure of at least about 400 mm $H_2O$ at increments of about 20 mm $H_2O$. In an exemplary embodiment, the valve element includes an aperture, a ball disposed within the aperture and having a diameter greater than a diameter of the aperture, and a biasing member effective to bias the ball against the aperture at the threshold pressure. The valve element can also include an adjustment mechanism that is coupled to the biasing member and that is effective to selectively adjust the threshold pressure. The biasing member can be, for example, a spring extending between the cam and the ball, and the adjustment mechanism can be, for example, a cam mechanism having a plurality of steps formed thereon, each step corresponding to a threshold pressure.

The present invention also provides a method for treating hydrocephalus. In one embodiment, the method includes the steps of implanting a valve in a patient's body such that fluid in the patient's body can flow into an inlet in the valve and out through an outlet in the valve, and periodically and repeatedly increasing a threshold pressure of the valve up to at least about 400 mm $H_2O$ at increments in the range of about 10 mm $H_2O$ to 40 mm $H_2O$ such that fluid can only flow through the valve when a fluid pressure at the inlet is greater than the threshold pressure of the valve element. Preferably, the threshold pressure of the valve is increased from an initial pressure in the range of about 30 mm $H_2O$ to 200, and more preferably from about 30 mm $H_2O$ to 140 mm $H_2O$, to a final pressure in the range of about 200 mm $H_2O$ to 500 mm $H_2O$, and more preferably from about 300 mm $H_2O$ to 400 mm $H_2O$. In an exemplary embodiment, the threshold pressure of the valve is increased in increments of about 5% of the total valve operating pressure range.

In yet another embodiment, a method for treating hydrocephalus is provided and it includes the step of implanting a shunt system having a proximal catheter disposed within a ventricular cavity of the patient's brain, a distal catheter installed at a remote location in the patient's body where fluid is to be reintroduced, and a valve disposed between the proximal and distal catheters and adapted to control a rate of fluid flow from the ventricular cavity to the remote location. A threshold pressure of the valve is then set such that fluid can only flow through the valve when a fluid pressure in the first catheter is greater than the threshold pressure of the valve. The threshold pressure is then periodically increased at increments in the range of about 10 mm $H_2O$ to 40 mm $H_2O$ until a pressure greater than about 400 mm $H_2O$ is achieved such that the shunt system can be removed and the patient is cured of hydrocephalus.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention generally provides a valve for use in a shunt system to drain fluid from one part of a patient's body to another. While the valve is primarily described in connection with a shunt system for treating hydrocephalus, the valve can be used in other types of implantable devices for controlling fluid flow. In an exemplary embodiment, the valve is operable at a threshold pressure that is selectively adjustable up to at least about 400 mm $H_2O$ at increments in the range of about 10 mm $H_2O$ to 40 mm $H_2O$. The ability of the valve to operate at a high threshold pressure and to be adjusted at relatively small and precise increments renders the valve particularly advantageous for use in younger hydrocephalus patients. In particular, the threshold pressure of the valve can be gradually increased in small increments over a period of time to reduce the amount of fluid flowing through the valve and slowly force the patient's own resorption system to circulate cerebrospinal fluid and. At high operating pressures of at least about 400 mm $H_2O$, shunt independence can be achieved thereby allowing the shunt to be successfully removed.

Figure 1:
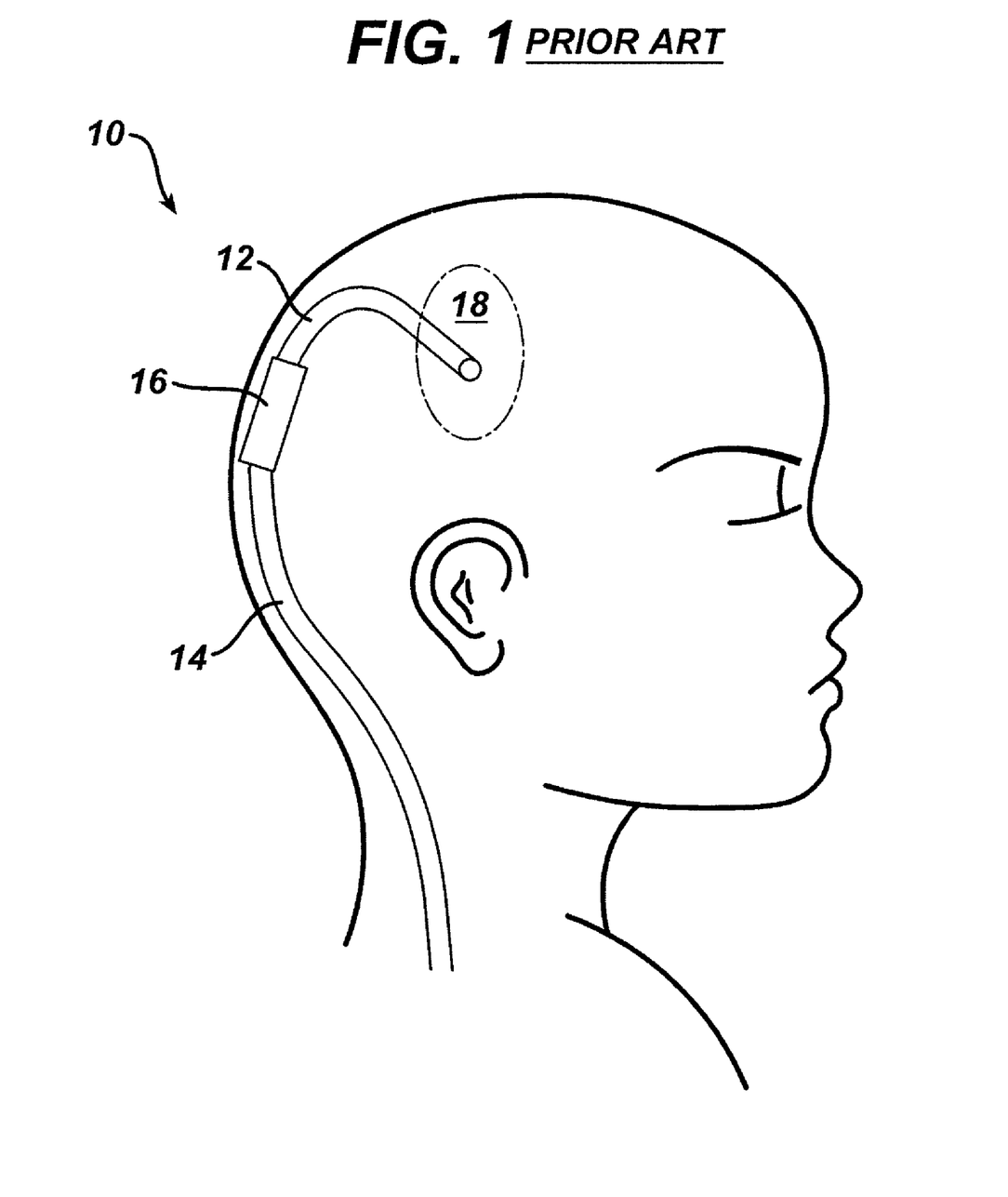
FIG. 1 is partially cross-sectional side view of a prior art hydrocephalus shunt system implanted within a ventricle of a patient's brain.

FIG. 1 illustrates a prior art shunt system 10. As shown, the system 10 generally includes a proximal catheter 12, also referred to as a ventricular catheter, that is disposed within a ventricular cavity 18 of the patient's brain, a distal catheter 14, also referred to as a drainage catheter, that is installed at a remote location, e.g., the circulatory system, in the patient's body where fluid is to be reintroduced, and a valve 16 that is disposed between the proximal and distal catheters 12, 14 and that is adapted to control a rate of fluid flow from the ventricular cavity 16 to the remote location. The system 10 also includes an external programming device (not shown) for adjusting a threshold pressure at which fluid can flow from the proximal catheter 12 through the valve 16 to the distal catheter 14 to be delivered at the remote location.

FIGS. 2A-2D illustrate one embodiment of a prior art externally programmable valve system 50 and an external programming device 52 for adjusting a threshold pressure at which fluid begins to flow through the device. The valve 50 and external programming device 52 are described in more detail in U.S. Pat. Nos. 3,886,948, 4,332,255, 4,387,715, 4,551,128, 4,595,390, 4,615,691, 4,772,257, and 5,928,182, all of which are hereby incorporated by reference.

Figure 2A:
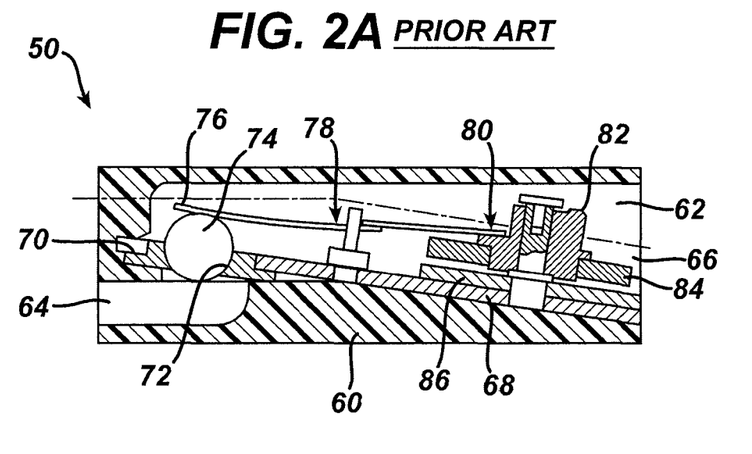
FIG. 2A is a side, sectional view of a prior art externally programmable shunt valve.
Figure 2B:
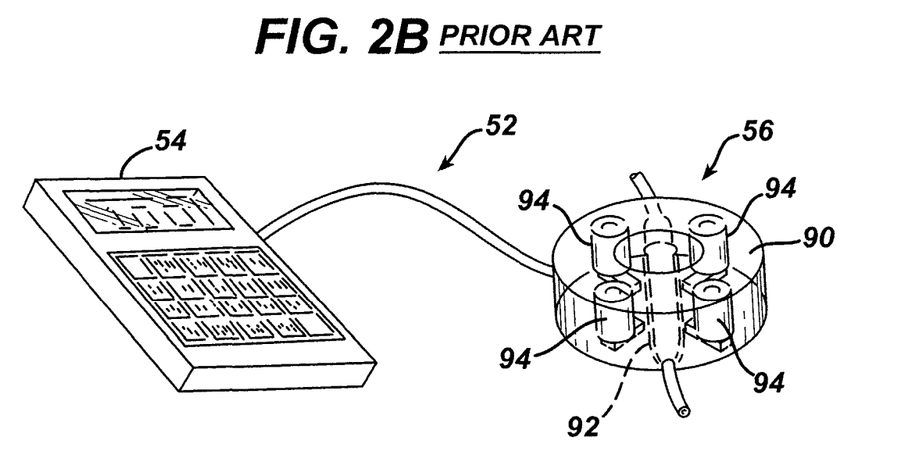
FIG. 2B is perspective view of a prior art programmer for programming the prior art shunt valve of FIG. 2A.

As shown in FIG. 2A, the shunt valve 50 generally includes a valve body 60 defining a chamber 62 with an inlet 64 and an outlet 66. A support plate 68 is disposed within the valve body 60 and it separates the inlet 64 from the outlet 66. An aperture 70 is formed in the support plate 68 at one end thereof and it defines a valve seat 72 for seating a ball 74 in sealing engagement therewith. The valve seat 72 is substantially cone-shaped and it has a cone angle of about 60°. The ball 74 and the aperture 70 can be formed from a polished hard material, preferably a ruby or synthetic sapphire, to ensure an effective seal when the ball 74 is seated in the valve seat 72, and to lessen the tendency for the ball 74 to become stuck in the seat 72. As can be seen more clearly in FIG. 2D, the spherical ball 74 has a diameter $d_b$ that is larger than the diameter $d_a$ of the aperture 70, but that is substantially the same as a radius of curvature of the valve seat 72. In particular, the spherical ball has a diameter $d_b$ that is about 1.57 mm (0.062 inches), which is substantially the same as the radius of curvature of the valve seat 72, but which is greater than the diameter $d_a$ of the aperture 70, which is about 1.45 mm (0.053 inches).

The valve 50 also includes a biasing element, e.g., spring 78, having a first end 76 that biases the ball 74 into the valve seat 72 to prevent fluid flow through the aperture 70, and thus through the valve 50. The second end 80 of the spring 78 is coupled to a cam mechanism 82 that is effective to change the biasing force of the spring 78 against the ball 74. The cam mechanism 82 includes a circular staircase of eighteen steps 83, each being grooved so as to have a V-shape cross section. The end 80 of the spring 78 that is position on the steps 83 also has a similar V-shape chosen to mate with the V-shape of steps 83. At each end of the staircase 83 a barrier (not shown) is provided. This confines rotation of the cam 82 to slightly less than one revolution. The V-shape of steps 83 act as detents to keep the cam 82 in precisely one of eighteen possible angular positions. That means that the vertical position of free end 80 of the spring 78 is always at precisely one of eighteen different values. In use, the cam 82 is rotated to increase or decrease a height of the spring 78 at a second end 80, thereby increasing or decreasing the pressure applied to the ball 74 by the first end 76 of the spring 78. The biasing force provided by the spring 78 therefore determines the threshold pressure that must be overcome in order to separate the ball 74 from the valve seat 72 to allow fluid flow into the chamber 62 and out the outlet 66 of the valve 50.

Referring back to FIG. 2A, the cam 82 is disposed in a centrally located hole in a rotor 84 which includes a plurality of permanent magnetic poles of alternate polarity. At any one angular position, a pole exposed on the top side has an opposite pole on the other side. Below the rotor 84, four stator elements are fixed in a stator member 86. The stator elements are formed from a magnetically soft and permeable material. The stator elements are shaped to conform to the rotor 84 elements.

In use, the shunt valve 50 is surgically implanted under the scalp of a patient and it is coupled to proximal and distal catheters, as shown in FIG. 1. After surgical implantation of the shunt valve 50 under the scalp of a patient, a threshold pressure of the valve 50 can be adjusted by using the programmer 52 shown in FIG. 2B. The programmer 52 includes a control device 54 for selecting a threshold pressure and a programming element 56 that is configured to be placed over the valve. In particular, the programming element 56 includes a housing 90 with a groove 92 that is adapted to conform to a protrusion on the scalp caused by the implanted shunt valve 50. Thus, in use, an operator maneuvers the programming element 56 so that the scalp protrusion is within the groove 92. Thereafter, a series of electromagnets 94 disposed about a central axis are sequentially energized to apply a pulsed magnetic field to the stepper motor and cause the rotor 84 to rotate. This causes the cam 82 to rotate to one of eighteen positions, therefore adjusting the pressure applied to the ball 74 by the first end 76 of the spring 78. In this manner, the threshold pressure of the shunt valve 50 is adjusted. Due to the size of the aperture 70, the size of the ball 74, and the number of steps 83 on the cam 82, the valve 50 can be adjusted in increments of 10 mm $H_2O$ to one of eighteen pressures ranging from 20 mm $H_2O$ to 190 mm $H_2O$.

Figure 3A:
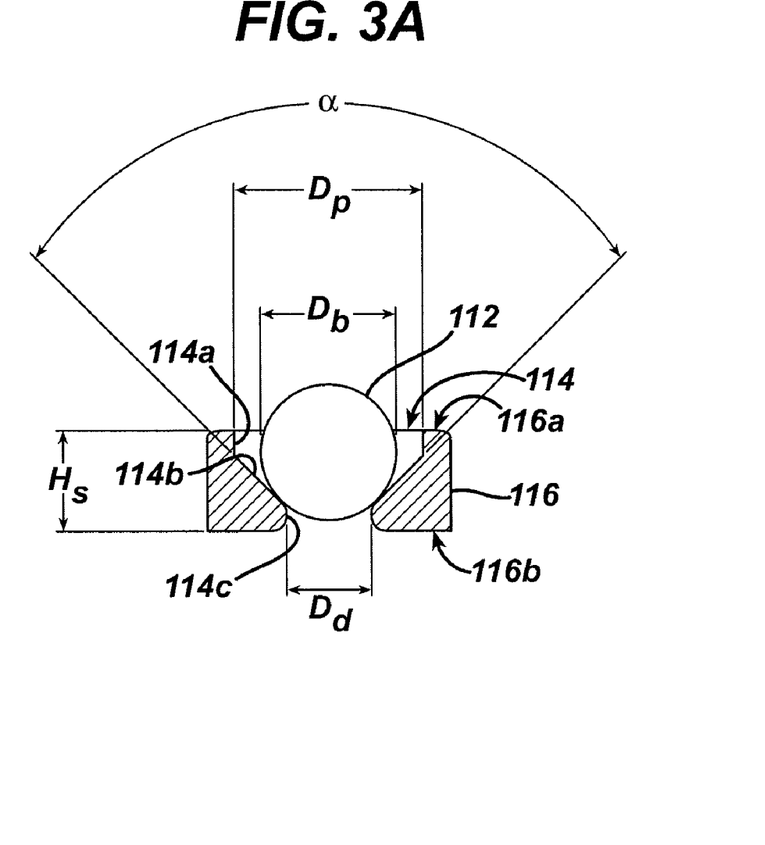
FIG. 3A is a cross-sectional side view illustration of one embodiment of support plate having a ball-in-cone valve element in accordance with the present invention for use in a hydrocephalus valve.
Figure 3B:
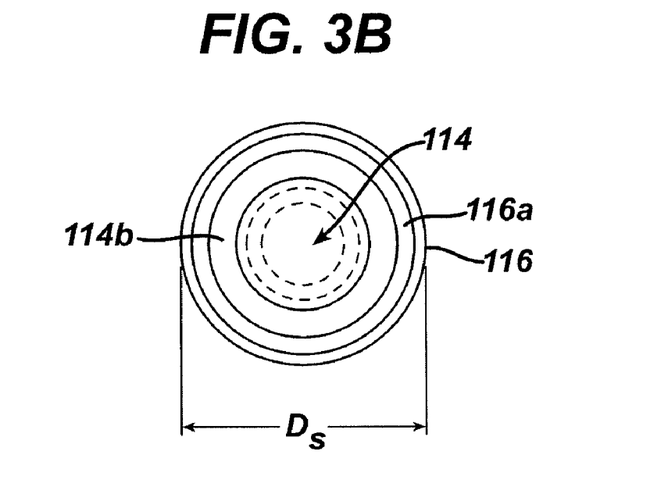
FIG. 3B is a top view of the support plate shown in FIG. 3A.

FIGS. 3A and 3B illustrate a portion of a shunt valve in accordance with the present invention. In this embodiment, the valve is configured to allow the threshold pressure to be adjusted up to a threshold pressure of at least about 400 mm $H_2O$, and more preferably about 500 mm $H_2O$. The threshold pressure is also preferably adjustable in increments ranging from 10 mm $H_2O$ to 40 mm $H_2O$, and more preferably in increments of about 20 mm $H_2O$.

Referring to FIGS. 3A and 3B, a support plate 116, similar to support plate 68 of valve 50. The support plate 116 can vary in shape and size, but in an exemplary embodiment, as shown, the support plate 116 has a substantially cylindrical shape with a diameter $D_s$ that is preferably in the range of about 1.5 mm to 3.0 mm, and more preferably that is about 2.2 mm, and a height $H_s$ that is in the range of about 0.7 mm to 1.5 mm, and more preferably that is about 0.9 mm.

As further shown in FIGS. 3A and 3B, the support plate 116 includes an aperture 114 formed therein for seating a ball 112. The aperture 114 includes a proximal portion or chamfer 114a, a cone-shaped or mid-portion 114b which defines the valve seat for seating the ball 112, and a distal, substantially cylindrical portion 114c. As shown, the chamfer 114a is substantially cylindrical such that the sidewalls extend parallel to one another, and it extends from the mid-portion 114b to a proximal surface 116a of the support plate 68. The chamfer 114a is particularly advantageous in that it provides performance characteristics, such as flow regulation and anti-reflux, while preventing the ball from becoming unseated during normal valve operations (i.e. physiologic flow conditions).

The size of the aperture 114 and ball 112 can vary, but in an exemplary embodiment, the proximal portion has a diameter $D_p$ that is in the range of about 1.6 mm (0.063 inches) to 1.8 mm (0.071 inches), and more preferably that is about 1.7 mm (0.067 inches), and the distal portion 114c has a diameter $D_d$ that is substantially smaller than the diameter $D_p$ of the proximal portion 114a. In an exemplary embodiment, the distal portion 114c has a diameter $D_d$ that is in the range of about 0.70 mm (0.027 inches) to 0.80 mm (0.031 inches), and more preferably that is about 0.762 mm (0.030 inches). The ball 112 has a diameter $D_b$ that is less than the diameter $D_p$ of the proximal portion 114a, but that is greater than the diameter $D_d$ of the distal portion 114c. In an exemplary embodiment, the ball 112 has a diameter $D_b$ that is greater than 0.8 mm (0.031 inches), and more preferably that is about 1.2 mm (0.047 inches).

The mid-portion 114b has sidewalls that extend at an angle α relative to one another, and in an exemplary embodiment, the cone angle α between the sidewalls is greater than about 70°, and more preferably it is about 95°. As a result, the ball 112 will not extend through the distal portion 114c and beyond a distal surface 116b of the support plate 116, but rather it will rest substantially within the mid-portion 114b to seal the aperture 114.

Figure 2C:
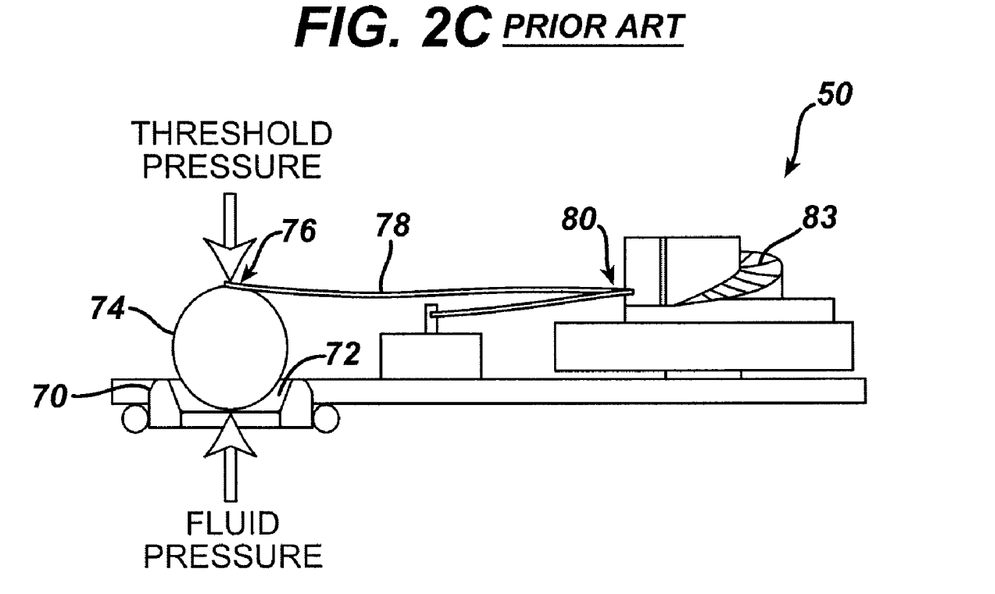
FIG. 2C is a side view illustration of the valve element of the externally programmable shunt valve shown in FIG. 2A.
Figure 2D:
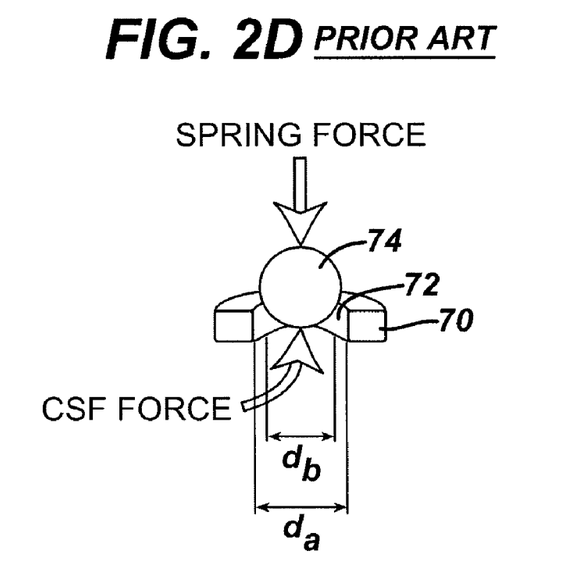
FIG. 2D is a cross-sectional side view illustration of the ball-in-cone portion of the externally programmable shunt valve shown in FIG. 2A.

The ball 112 and aperture 114 can be used in a variety of programmable valves, but in an exemplary embodiment they are used with a valve similar to valve 50 shown in FIGS. 2A, 2C, and 2D. In use, where the ball 112 has an exemplary diameter $D_b$, as noted above, and the aperture 114 has the shape and sizes noted above, rotation of the cam 82 to one of the eighteen steps 83 will be effective to adjust the pressure up to a threshold pressure of at least about 400 mm $H_2O$, and more preferably about 500 mm $H_2O$. By way of non-limiting example, where the maximum threshold pressure is 400 mm $H_2O$, and the initial pressure is set at about 60 mm $H_2O$, each step 83 on the cam 82 will change the pressure in increments of 20 mm $H_2O$. The incremental changes in the threshold pressure can, however, vary depending on the size of the ball 112 and aperture 114, as well as the height of the steps 83. In an exemplary embodiment, the threshold pressure can be adjusted in increments of about 5% of the total valve operating pressure range, or in increments of about 10 mm $H_2O$ to 40 mm $H_2O$ up to a pressure of at least about 400 mm $H_2O$, and more preferably about 500 mm $H_2O$.

In use, the ability of the valve to operate at a high threshold pressure of about 200 mm H$_2$O to 500 mm H$_2$O can be used to achieve shunt independence. The procedure begins by first setting the threshold pressure of the valve to a desired level according to the circumstances of the case, and then surgically implanting the valve in a patient following well-known procedures. Further adjustments in pressure can be made at subsequent times, as necessary. The threshold pressure is then periodically (e.g., 1 month after initial operation to 2-3 years) increased in small increments (e.g., 10 mm H$_2$O to 40 mm H$_2$O) to force the patient's own resorption system to circulate the CSF. Once a pressure of about 400 mm H$_2$O or greater is achieved, the valve is substantially in an off position, indicating that the patient's own resorption system is circulating cerebrospinal fluid. Shunt independent is therefore achieved, thus allowing the shunt to be successfully removed.

A person skilled in the art will appreciate that while a ball-in-cone valve mechanism is disclosed, the valve element can have a variety of configurations and virtually any valve mechanism know in the art can be used in accordance with the present invention. The valve is preferably, however, configured to remain closed until a fluid pressure differential between the inlet of the valve and the outlet of the valve exceeds a certain selected valve opening pressure. By way of non-limiting example, other suitable valve elements include a tapered pin and aperture, a sliding shutter, a shutter/gate mechanism, and a ball-in-cone construct.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A valve for use in treating hydrocephalus, comprising:
a housing having an inlet and an outlet;
a valve element disposed within the housing and effective to allow fluid to flow from the inlet in the housing to the outlet in the housing when a fluid pressure at the inlet is greater than a threshold pressure of the valve element; and
an adjustment mechanism coupled to the valve element and effective to selectively adjust the threshold pressure up to a maximum threshold pressure of at least about 400 mm H$_2$O at increments of about 20 mm H$_2$O or less.

2. The valve of claim 1, wherein the threshold pressure is adjustable in increments of 20 mm H$_2$O.

3. The valve of claim 1, wherein the threshold pressure is adjustable in increments of about 5% of the maximum threshold pressure.

4. The valve of claim 1, wherein the threshold pressure is adjustable in substantially uniform increments.

5. The valve of claim 1, wherein the valve element comprises an aperture, a restricting element disposed within the aperture and having a width greater than a width of the aperture, and a biasing member coupled to the adjustment mechanism and effective to bias the restricting element against the aperture at the threshold pressure.

6. The valve of claim 5, wherein the restricting element comprises a ball having a diameter that is greater than a diameter of the aperture.

7. The valve of claim 5, wherein the adjustment mechanism comprises a cam mechanism having a plurality of steps formed thereon, each step corresponding to a threshold pressure.

8. The valve of claim 7, wherein the biasing member comprises a spring extending between the cam and the restricting element.

9. The valve of claim 7, wherein the cam mechanism includes a plurality of positions, each position corresponding to a predetermined threshold pressure.

10. The valve of claim 9, wherein each position comprises a step formed on the cam mechanism, and wherein the cam mechanism includes 18 steps.

11. The valve of claim 6, wherein the aperture includes a proximal cone-shaped portion adapted to seat the ball and having a chamfer formed along an edge thereof, and a distal substantially cylindrical portion.

12. The valve of claim 1, wherein the adjustment mechanism is adapted to be controlled by a magnet.

13. A valve for use in treating hydrocephalus, comprising:
an inlet and an outlet;
a valve element in communication with the inlet and outlet and effective to allow fluid to flow from the inlet to the outlet when a fluid pressure at the inlet is greater than a threshold pressure of the valve element, the threshold pressure being selectively adjustable up to a pressure of at least about 400 mm H$_2$O at increments of about 20 mm H$_2$O.

14. The valve of claim 13, wherein the valve element comprises an aperture, a ball disposed within the aperture and having a diameter greater than a diameter of the aperture, and a biasing member effective to bias the ball against the aperture at the threshold pressure.

15. The valve of claim 14, further comprising an adjustment mechanism coupled to the biasing member and effective to selectively adjust the threshold pressure.

16. The valve of claim 15, wherein the adjustment mechanism comprises a cam mechanism having a plurality of steps formed thereon, each step corresponding to a threshold pressure.

17. The valve of claim 16, wherein the biasing member comprises a spring extending between the cam and the ball.

18. The valve of claim 16, wherein the cam mechanism includes 18 steps.

19. The valve of claim 14, wherein the aperture includes a proximal cone-shaped portion adapted to seat the ball and having a chamfer formed along an edge thereof, and a distal substantially cylindrical portion.

20. The valve of claim 15, wherein the adjustment mechanism is adapted to be controlled by a magnet.

21. A method for treating hydrocephalus, comprising:
implanting a valve in a patient's body such that fluid in the patient's body can flow into an inlet in the valve and out through an outlet in the valve;
periodically and repeatedly increasing a threshold pressure of the valve up to at least about 400 mm H$_2$O at increments of about 20 mm H$_2$O or less such that fluid can only flow through the valve when a fluid pressure at the inlet is greater than the threshold pressure of the valve element.

22. The method of claim 21, wherein the threshold pressure is adjustable in substantially uniform increments.

23. The method of claim 21, wherein the threshold pressure of the valve is increased from an initial pressure in the range of about 30 mm H$_2$O to 200 mm H$_2$O to a final pressure in the range of about 200 mm H$_2$O to 500 mm H$_2$O.

24. The method of claim 21, wherein the threshold pressure of the valve is increased from an initial pressure in the range of about 30 mm H$_2$O to 140 mm H$_2$O to a final pressure in the range of about 300 mm H$_2$O to 400 mm H$_2$O.

25. The method of claim 21, wherein the threshold pressure of the valve is increased in increments of about 20 mm $H_2O$.

26. The method of claim 21, wherein the threshold pressure of the valve is increased in increments of about 5% of the final pressure.

27. The method of claim 21, wherein the valve includes an aperture, a ball disposed within the aperture and having a diameter greater than a diameter of the aperture, and a biasing member effective to bias the ball against the aperture at the threshold pressure.

28. The method of claim 27, wherein the step of increasing a threshold pressure of the valve comprises rotating a cam mechanism coupled to the biasing member to increase a biasing pressure of the ball against the aperture.

29. The method of claim 28, wherein the cam mechanism includes a plurality of steps formed thereon, each step corresponding to a threshold pressure.

30. The method of claim 29, wherein the cam mechanism includes 18 steps.

31. The method of claim 27, wherein the aperture includes a proximal cone-shaped portion adapted to seat the ball and having a chamfer formed along an edge thereof, and a distal substantially cylindrical portion.

32. A method for treating hydrocephalus, comprising:
implanting a shunt system in a patient's body, the shunt system having a proximal catheter disposed within a ventricular cavity of the patient's brain, a distal catheter installed at a remote location in the patient's body where fluid is to be reintroduced, and a valve disposed between the proximal and distal catheters and adapted to control a rate of fluid flow from the ventricular cavity to the remote location;
setting a threshold pressure of the valve such that fluid can only flow through the valve when a fluid pressure in the first catheter is greater than the threshold pressure of the valve; and
periodically increasing the threshold pressure of the valve at increments of about 20 mm $H_2O$ or less until a pressure greater than about 400 mm $H_2O$ is achieved such that the shunt system can be removed.

33. The method of claim 32, wherein the threshold pressure of the valve is increased from an initial pressure in the range of about 30 mm $H_2O$ to 200 mm $H_2O$ to a final pressure in the range of about 200 mm $H_2O$ to 500 mm $H_2O$.

34. The method of claim 32, wherein the threshold pressure of the valve is increased from an initial pressure in the range of about 30 mm $H_2O$ to 140 mm $H_2O$ to a final pressure in the range of about 300 mm $H_2O$ to 400 mm $H_2O$.

35. The method of claim 32, wherein the threshold pressure of the valve is increased in increments of about 20 mm $H_2O$.

36. The method of claim 32, wherein the valve includes an aperture, a ball disposed within the aperture and having a diameter greater than a diameter of the aperture, and a biasing member effective to bias the ball against the aperture at the threshold pressure.

37. The method of claim 36, wherein the step of increasing a threshold pressure of the valve comprises rotating a cam mechanism coupled to the biasing member to increase a biasing pressure of the ball against the aperture.

38. The method of claim 37, wherein the cam mechanism includes a plurality of steps formed thereon, each step corresponding to a threshold pressure.

39. The method of claim 38, wherein the cam mechanism includes 18 steps.

40. The method of claim 36, wherein the aperture includes a proximal cone-shaped portion adapted to seat the ball and having a chamfer formed along an edge thereof, and a distal substantially cylindrical portion.

* * * * *